United States Patent
Park et al.

(10) Patent No.: US 8,673,605 B2
(45) Date of Patent: Mar. 18, 2014

(54) METHOD FOR INDUCING DIFFERENTIATION OF ADULT STEM CELLS AND NERVE CELLS USING ELECTROMAGNETIC FIELD

(75) Inventors: Jung-Keug Park, Seoul (KR); Sung Min Kim, Seoul (KR); Soo Chan Kim, Gyeonggi-do (KR); Moon Young Yoon, Seoul (KR); Hyun Jin Cho, Seoul (KR); Young-Kwon Seo, Seoul (KR); Hee Hoon Yoon, Gyeonggi-do (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 13/702,975

(22) PCT Filed: Jun. 8, 2011

(86) PCT No.: PCT/KR2011/004190
§ 371 (c)(1),
(2), (4) Date: Feb. 19, 2013

(87) PCT Pub. No.: WO2012/053718
PCT Pub. Date: Apr. 26, 2012

(65) Prior Publication Data
US 2013/0202565 A1    Aug. 8, 2013

(30) Foreign Application Priority Data
Oct. 19, 2010   (KR) .................. 10-2010-0101651

(51) Int. Cl.
*A01N 63/00* (2006.01)
*C12N 13/00* (2006.01)
*C12N 5/0793* (2010.01)

(52) U.S. Cl.
CPC ............ *C12N 5/0619* (2013.01); *C12N 13/00* (2013.01); *C12N 2506/1346* (2013.01)
USPC .................................... 435/173.1; 435/173.8

(58) Field of Classification Search
None
See application file for complete search history.

(56) References Cited

U.S. PATENT DOCUMENTS

| 2005/0075679 | A1 | 4/2005 | Gliner et al. |
| 2006/0205993 | A1 | 9/2006 | Fischell et al. |
| 2007/0065941 | A1 | 3/2007 | Kondo et al. |
| 2010/0239544 | A1* | 9/2010 | Simon .......................... 424/93.7 |

FOREIGN PATENT DOCUMENTS

| JP | 2008543388 | 6/2006 |
| KR | 20050044849 | 5/2005 |
| KR | 20060108451 | 10/2006 |
| KR | 20080068351 | 7/2008 |
| KR | 20090055691 | 6/2009 |

OTHER PUBLICATIONS

L.-Yi. Sun, D.-K. Hsieh, T.-C. Yu, H.-T. Chiu, S.-F. Lu, G.-H. Luo, T.K. Kuo, O.K. Lee, and T.-W. Chiou, "Effect of Pulsed Electromagnetic Field on the Proliferation and Differentiation Potential of the Human Bone Marrow Mesenchymal Stem Cells", Bioelectromagnetics 2009, vol. 30, pp. 251-260.*
Boucherie, C., and Hermans E., "Adult Stem Cell Therapies for Neurological Disorders: Benefits Beyond Neuronal Replacement?", Journal of Neuroscience Research 2009, vol. 87, pp. 1509-1521.*
Matos, M.A., and Cicerone, M.T., "Alternating Current Electric Field Effects on Neural Stem Cell Viability and Differentiation", Biotechnology Progress 2010, vol. 26, pp. 664-670.*
Alexanian et al., "In Vitro and In Vivo Charactreization of Neurally Modified Mesenchymal Stem Cells Induced by Epigenetic Modifiers and Neural Stem Cell Environment", Stem Cells and Development, vol. 17:1123-1130 (2008).
Anghileri et al., "Neuronal Differentiation Potential of Human Adipos-Derived Mesenchymal Stem Cells" Stem Cells and Development, vol. 17:909-916 (2008).
Croft et al., "Mesenchymal Stem Cells Expressing Neural Antigens Instruct a Neurogenic Cell Fate on Neural Stem Cells", Experimental Neurology, vol. 216:329-341 (2009).
Hofstetter et al, "Allodynia Limits the Usefulness of Intraspinal Neural Stem Cell Grafts; Directed Differentiation Improves Outcome", Nature Neuroscience, vol. 8(3):346-353 (Mar. 2005).
Kokai et al., "The Potential of Adipose-Derived Adult Stem Cells as a Source of Neuronal Progenitor Cells", American Society of Plastic Surgeons, vol. 116(5):1453-1460 (Nov. 23, 2004).
Kuh et al., "Functional Recovery Aftre Human Umbilical Cord Blood Cells Transplantation with Brain-Derived Neutrophic Factor into the Spinal Cord Injured Rat" Acta Neurochir, vol. 147:985-992 (2005).
Longhi et al., "Ex Vivo Gene Therapy Using Targeted Engraftment of NGF-Expressing Human NT2N Neurons Attenuates Cognitive Deficits Following Traumatic Brain Injury in Mice", Journal of Neurotrauma, vol. 21:1723-1736 (Nov. 12, 2004).
Xu et al., "Inhibition of Histone Deacetylase Activity in Reduced Oxygen Environment Enhances the Osteogenesis of Mouse Adipose-Derived Stromal Cells", Tissue Engineering: Part A, vol. 15(12):3697-3707 (Jul. 20, 2009).

* cited by examiner

Primary Examiner — Allison Ford
Assistant Examiner — Michelle F Paguio Frising
(74) Attorney, Agent, or Firm — Dardi & Herbert, PLLC.; Curtis B. Herbert

(57) ABSTRACT

The present invention relates to a method for differentiation of mesenchymal stem cells or dental pulp stem cells. More specifically, the invention relates to a method for differentiating stem cells to neural cells by applying mesenchymal stem cells or dental pulp stem cells with a low-frequency electromagnetic field. The differentiation method according to the present invention can induce differentiation even with low-cost mediums rather than induced neural differentiation mediums which are expensive due to addition of growth factors, and the neural cells differentiated according to the present invention may be useful for treatment of neurological brain diseases.

3 Claims, 12 Drawing Sheets

METHOD FOR INDUCING DIFFERENTIATION OF ADULT STEM CELLS AND NERVE CELLS USING ELECTROMAGNETIC FIELD

CROSS REFERENCE TO RELATED APPLICATIONS

This application is a national stage filing of PCT Application PCT/KR2011/004190 filed Jun. 8, 2011, which claims priority to Korean Patent Application No. 10-2010-0101651 filed Oct. 19, 2010, both of which applications are hereby incorporated by reference herein.

TECHNICAL FIELD

The present invention relates to a method for differentiation of mesenchymal stem cells or adult stem cells. More specifically, the present invention relates to a method for differentiating mesenchymal stem cells or adult stem cells into neural cells by applying an electromagnetic field of a specific frequency to the mesenchymal stem cells or adult stem cells.

BACKGROUND

Since neural cells have been used as a candidate material for treatment of cranial nerve diseases such as Alzheimer's disease, depression, Parkinson's disease, cerebral infarction, cerebral hemorrhage, spinal cord injuries, etc., extensive research related to neural cells has recently been actively conducted, and a number of papers and patents have been disclosed. However, the neural cells or neural stem cells are difficult to obtain, and thus many studies related to differentiation of mesenchymal stem cells, which are relatively easy to obtain, into neural cells have been conducted. According to Lauren's review paper (*Plast. Reconstr. Surg.* 116:1453, 2005), among six reports on differentiation of adipose-derived mesenchymal stem cells into neural cells in vitro by a chemical method, differentiated neural cells exhibiting functionally significant electrophysiological properties have been reported in one case. According to Arshak (*Stem Cells and Development*, 17: 1123-30, 2008), the differentiation of bone marrow-derived mesenchymal stem cells into neural cells was induced by chemical differentiation, and differentiated neuronal markers were investigated by immunohistochemistry, Western blot (B3T, GFAP, MAP-2, NeuN), (nerve growth factor (NGF), brain-derived neurotrophic factor (BDNF)), etc. to observe their properties, but the electrophysiological properties were not found. Research aimed at using mesenchymal stem cells in neurological treatment by mixed culture of neural cells or neural precursor cells has been conducted (Croft A P, *Exp. Neurol.*, 216(2): 329-41 (2009)), but it is practically impossible to obtain a sufficient amount of human neural cells or neural precursor cells used in the mixed culture. As another research direction, a study of inducing overexpression of neuronal genes using lentivirus to improve the differentiation has been conducted (Watson, D. J., *Journal of Neurotrauma*, 21:1723-36. (2004), Hofstetter, C., *Nature Neuroscience*, 8: 346-53. (2005)), but the safety of the virus has not been ensured, which makes it difficult to apply to cell therapy.

According to Kuh et al. (*Acta Neurochir* 147:985-992, 2005), at 8 weeks after transplantation of human umbilical cord blood cells into mice with spinal cord injury, similar results were observed in Basso, Beattie and Bresnahan (BBB) scores compared with the control group with media alone, and at 5 weeks after transplantation of human umbilical cord blood cells mixed with brain-derived neurotrophic factor (BDNF), similar results were obtained, from which it can be seen that the simple transplantation of stem cells has limitations. According to Rooney et al. (*Tissue Engineering Part A*, Mar. 31, 2009), after transplantation of glial cell line-derived neurotrophic factor (GDNF) genes into bone marrow-derived mesenchymal stem cells isolated from fluorescent labeled mice, it was observed that the stem cells into which the glial cell line-derived neurotrophic factor genes were introduced survived for 6 weeks. However, after transplantation of mesenchymal stem cells alone, the transplanted cells were not observed after 2 weeks, and thus it was reported that the transplantation of mesenchymal stem cells alone was insufficient for the treatment of spinal cord injury.

One known neurological treatment technique using electromagnetic field includes a system for applying a low-frequency of approximately 10 Hz to a patient's brain tissue, in which direct electrical stimulation is applied to electrodes implanted in or on the patient's brain to cause a magnetic field due to electrical currents (US20060205993). Zheng discloses a magnetic stimulation apparatus for central nervous system, in which the magnetic stimulation with a precise wave form, high frequency or a combination of a plurality of frequency components is used for improvement of brain function (JP2008-543388). Riken discloses a method for preparing neural cells by electric pulse treatment of embryonic stem cells (US20070065941). Gliner et al. disclose a method for preparing neural cells by electric pulse treatment of cells (US20050075679). However, the above techniques employ direct implantation of electrodes, which involve electrode implant surgery that causes pain to patients. In the case of embryonic stem cells, the possibility of tumor formation is raised, and there are limitations in their application to clinical trials.

SUMMARY

The present study is to use mesenchymal stem cells and adult stem cells as a cell therapy product for treatment of various neurological diseases, and the development of a new technique for differentiation of mesenchymal stem cells and adult stem cells into neural cells by a non-invasive method, not a chemical method, is required.

Technical Problem

The present inventors, recognizing the above-described problems and needs, made extensive efforts to develop a method for inducing differentiation of mesenchymal stem cells and adult stem cells, which are relatively easy to obtain, into neural cells so as to obtain neural cells or neural stem cells, which are difficult to obtain, and found that the treatment of stem cells with an electromagnetic field of a specific frequency can induce differentiation of the stem cells, thus completing the present invention.

Accordingly, an object of the present invention is to provide a method for differentiation of mesenchymal stem cells or adult stem cells into neural cells.

Another object of the present invention is to provide a composition for treatment of neurological diseases.

Technical Solution

To achieve the above objects, the present inventors provide a method for differentiation of mesenchymal stem cells or adult stem cells into neural cells by applying an electromagnetic field to the mesenchymal stem cells or adult stem cells.

The neural cells may comprise astrocytes and oligodendrocytes.

Preferably, the electromagnetic field may be applied at a frequency of 1 to 1000 Hz.

Preferably, the electromagnetic field may be applied at a intensity of 1 to 5 mT.

The mesenchymal stem cells may be derived from bone marrow, adipose, or umbilical cord.

Moreover, the present invention provides a composition for treatment of neurological diseases comprising the neural cells differentiated by the above-described method.

The neurological diseases may comprise Alzheimer's disease, depression, Parkinson's disease, cerebral infarction, cerebral hemorrhage, or spinal cord injury.

Advantageous Effects

The method and apparatus for differentiation of stem cells using electromagnetic fields according to the present invention can induce differentiation of adult stem cells into neural cells using low-frequency waves, which makes it possible to easily obtain neural cells or neural stem cells, which are difficult to obtain, can induce neuronal differentiation with neuronal differentiation induction media even under conditions of low-cost media, not with the neuronal differentiation induction media which are expensive due to the addition of growth factors, and thus can be effectively used for the treatment of cranial nerve diseases such as Alzheimer's disease, depression, Parkinson's disease, cerebral infarction, cerebral hemorrhage, spinal cord injury, etc.

DETAILED DESCRIPTION

The present invention relates to a method for differentiation of mesenchymal stem cells or adult stem cells into neural cells by applying an electromagnetic field to the stem cells.

The electromagnetic wave used in the present invention is a phenomenon in which an electromagnetic field, whose intensity changes periodically, propagates through space, and is also called an electric wave, a low-frequency electric wave refers to a wave with a low frequency, typically below 10 kHz.

The "mesenchymal stem cells" used in the present specification may be derived from embryo, adult tissue, bone marrow, adipose, or umbilical cord. The stem cells of the present invention also include adult stem cells, and the adult stem cells may preferably be dental pulp stem cells.

Stem cells are undifferentiated cells that can divide over a long period of time, can self-renew, and can differentiate into various types of cells when certain conditions are given. Stem cells are divided into embryonic stem cells and adult stem cells according to their origin of tissue. The potential of adult stem cells is less than that of embryonic stem cells, but has no ethical issues, and thus many therapeutic agents have been studied on adult stem cells having no side effects.

Specifically, in the present invention, adult stem cells are used, which may be commercially available or isolated from living tissues.

The neural cells include astrocytes, oligodendrocytes, and neurons.

According to the present invention, only when the electromagnetic field of a specific frequency is applied to mesenchymal stem cells or adult stem cells, they can differentiate into neural cells.

The present invention has developed a technique for inducing neuronal differentiation of adult stem cells using electromagnetic fields in vitro, and the electromagnetic fields may be low-frequency electromagnetic field having a frequency of 1 to 1000 Hz, and more preferably 1 to 200 Hz at a flux density of 1 to 10 mT, and more preferably 1 to 5 mT.

Figure 1:
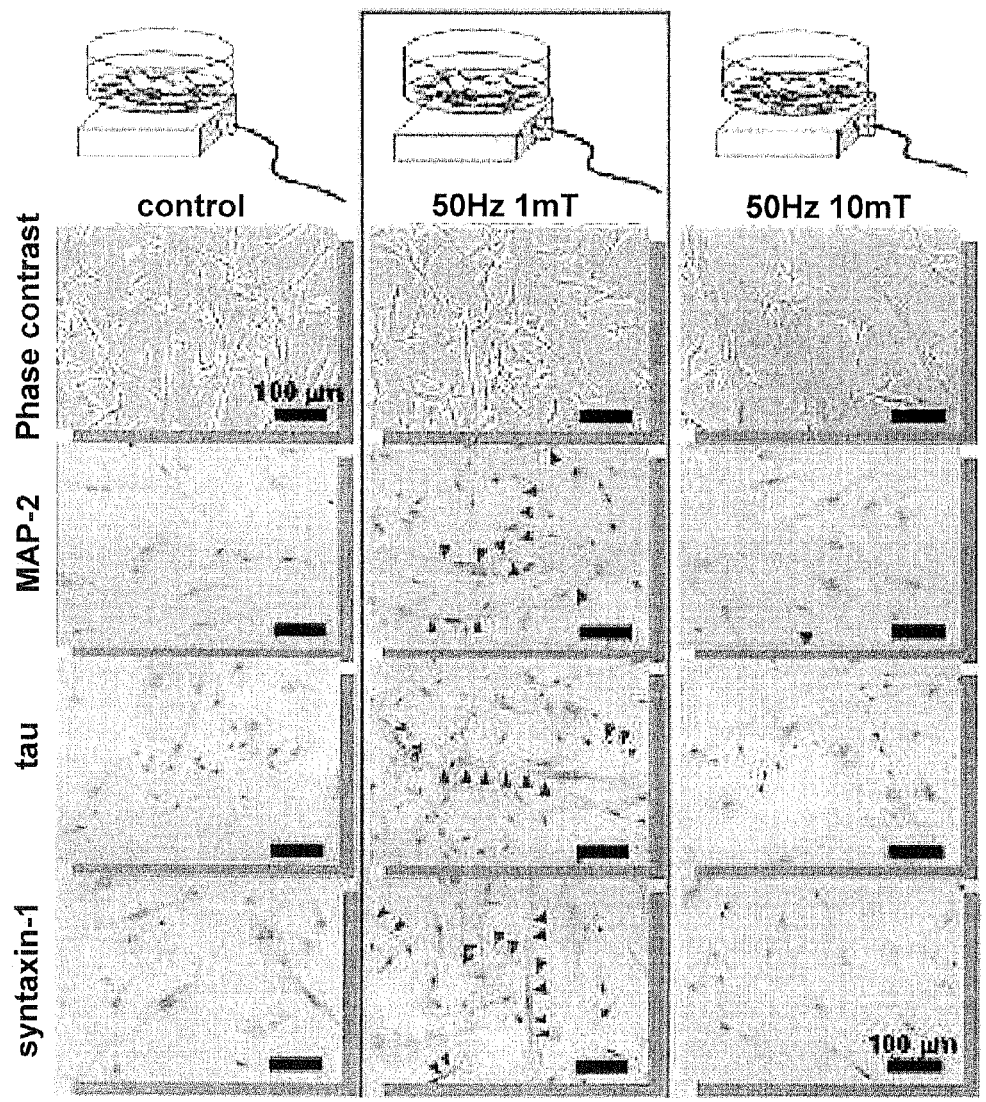
FIG. 1 shows the results of an experiment on the conditions for inducing neuronal differentiation of adult stem cells, including the observation of morphological changes of cells after in vitro exposure to electromagnetic field and the expression of neuronal markers (MAP-2, tau, and syntaxin-1).

According to an embodiment of the present invention, as shown in FIG. 1, as a result of immunohistochemical staining after applying electromagnetic fields for 7 days, it was observed that the expression of MAP-2, and tau was significantly increased at 1 mT and 50 Hz and the expression was not detected at 10 mT with the same frequency. This means that the cells differentiate only at specific frequency and flux density.

Figure 2:
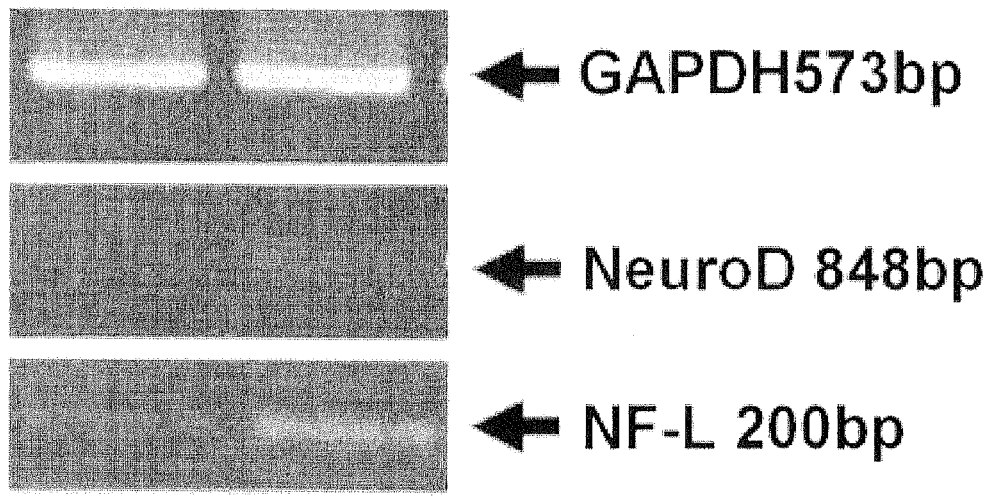
FIG. 2 shows the results of expression of neuronal mRNAs after inducing neuronal differentiation of adult stem cells.
Figure 3:
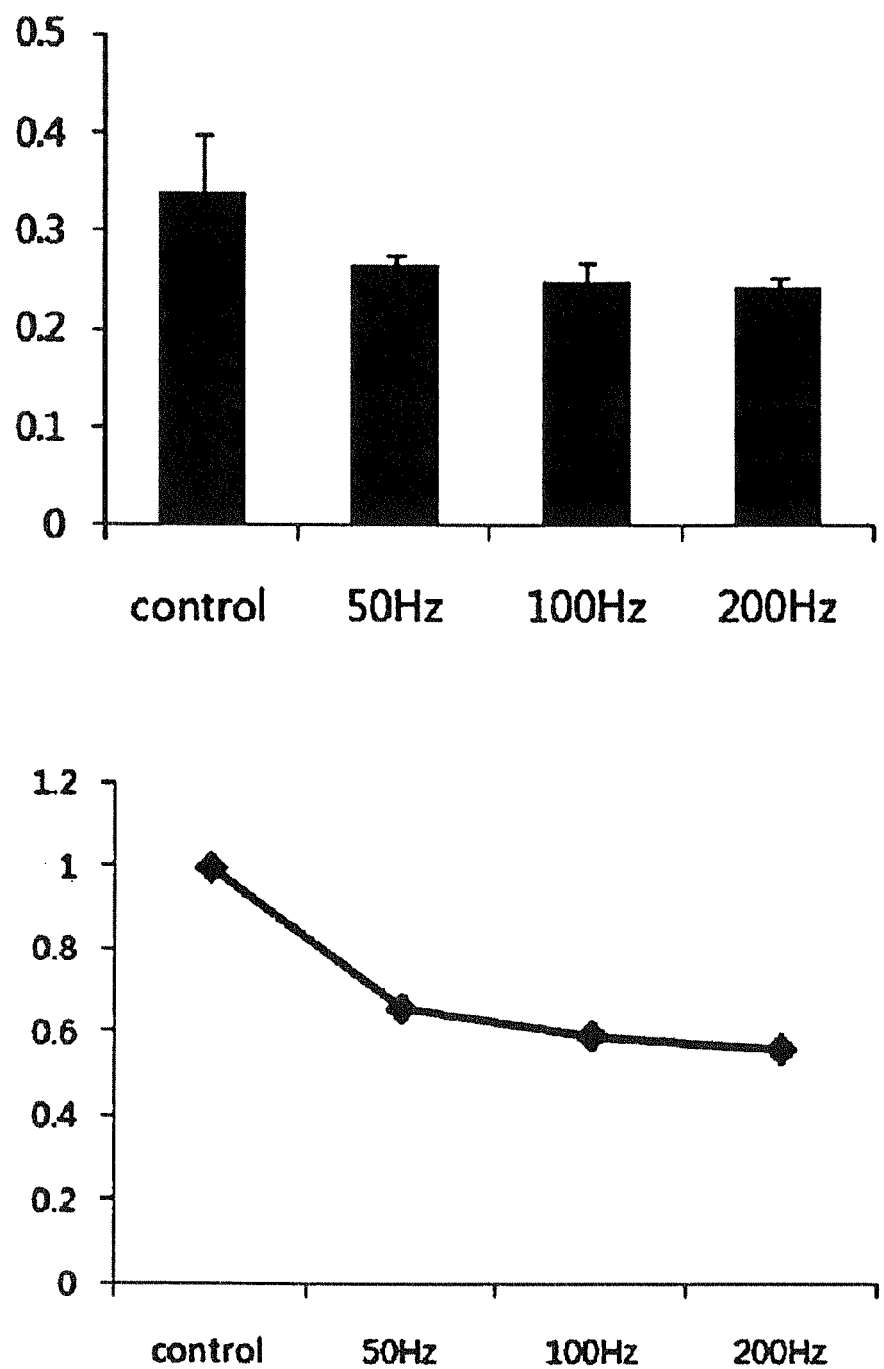
FIG. 3 shows the inhibition of proliferation of mesenchymal stem cells after exposure to 50 Hz, 100 Hz, and 200 Hz electromagnetic fields, determined using BrdU assay and cell counting method.
Figure 6:
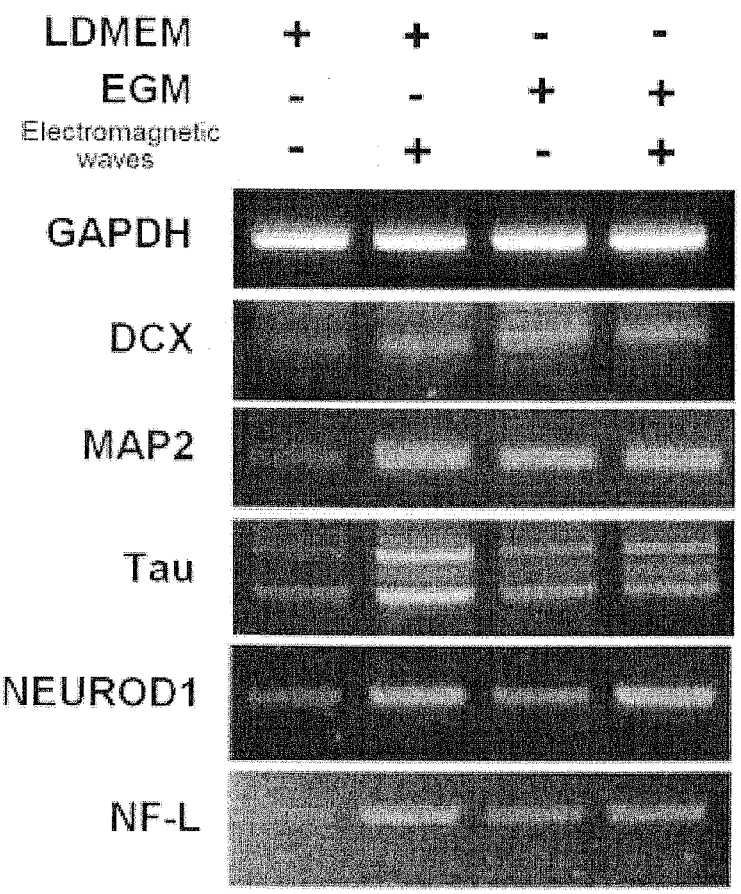
FIG. 6 shows the expression of neuronal markers including MAP2, tau, NeuroD1, DCX, and NF-L by 50 Hz electromagnetic fields.
Figure 7:
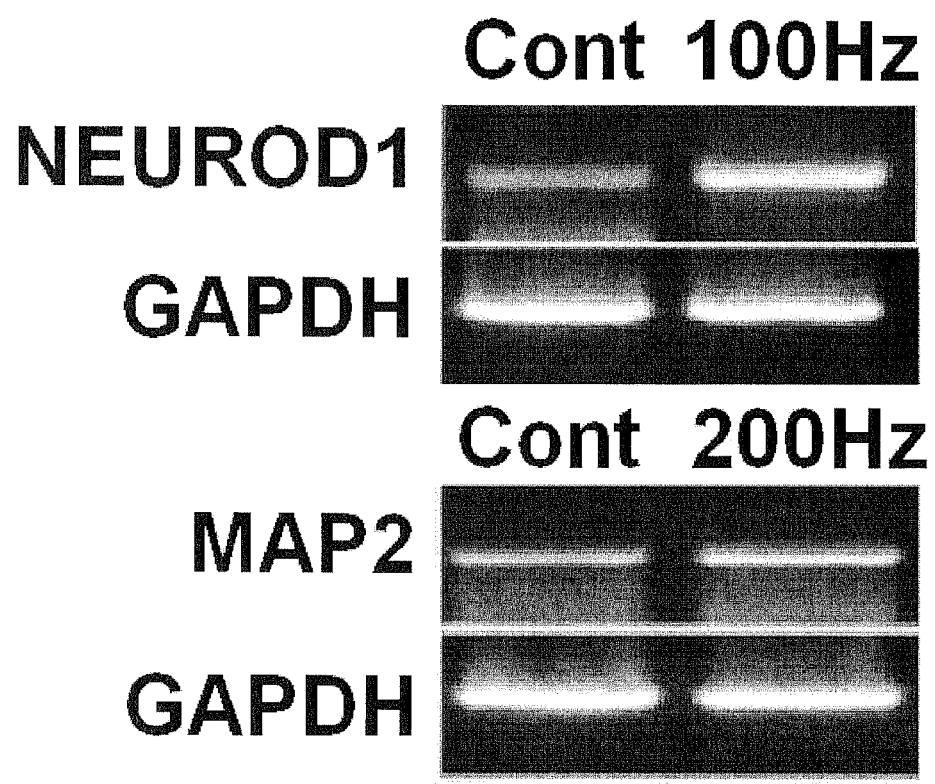
FIG. 7 shows the expression of neuronal markers including MAP2 and NeuroD1 by 100 Hz and 200 Hz electromagnetic fields.
Figure 8:
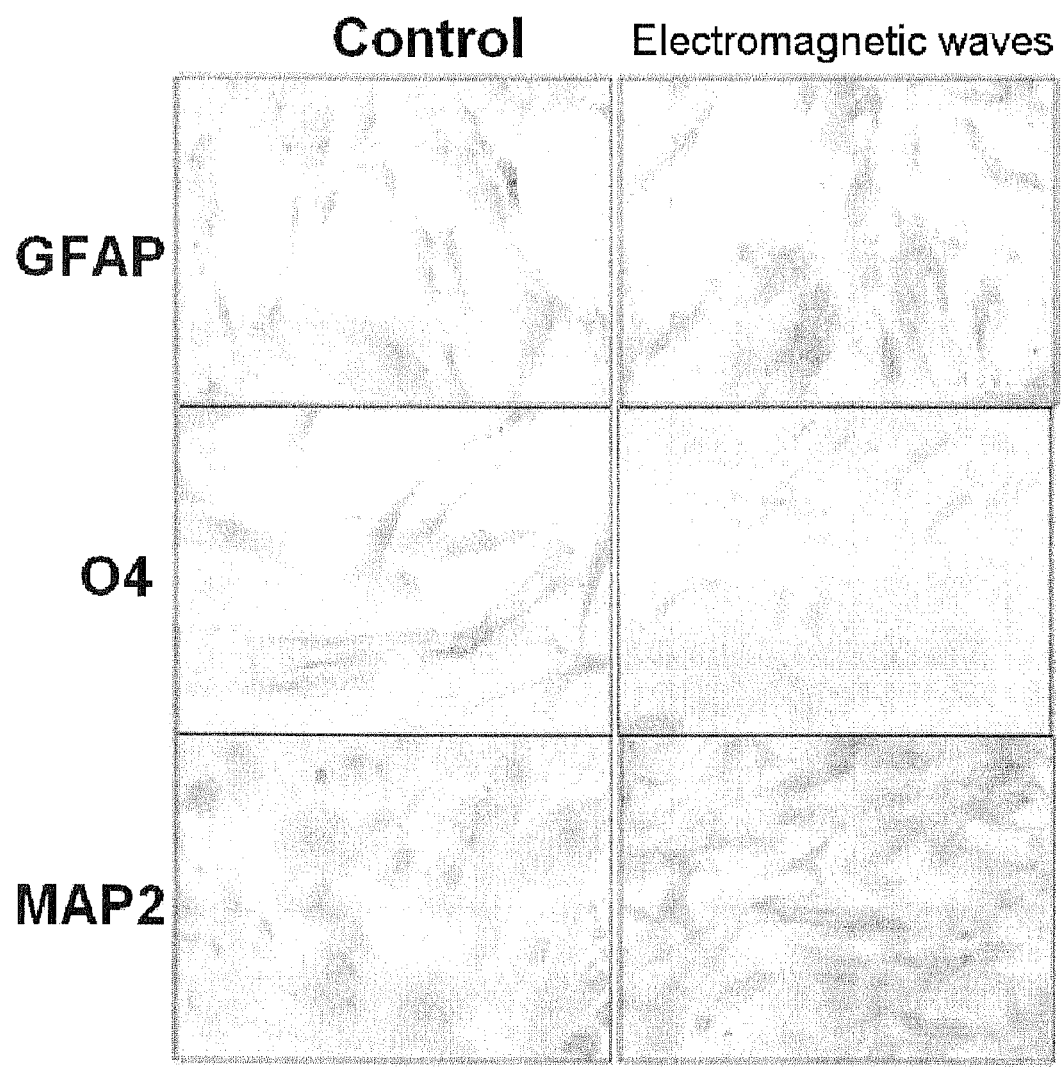
FIG. 8 shows the differentiation of mesenchymal stem cells into astrocytes and oligodendrocytes as well as neural cells by 50 Hz electromagnetic fields, determined using immunohistochemical staining.
Figure 9:
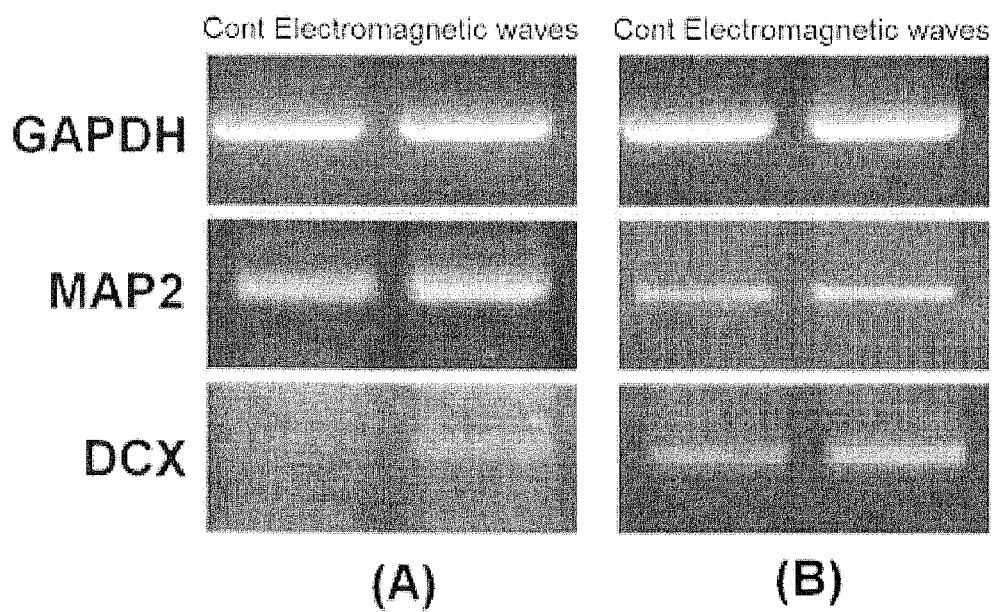
FIG. 9 shows the expression of neuronal markers including MAP2 and DCX by exposure of umbilical cord-derived stem cells (A) and adipose-derived stem cells (B) to 50 Hz electromagnetic fields (1 mT).

According to FIG. 2, after inducing differentiation by exposure to low-frequency electromagnetic field for 7 days, neuronal mRNAs such as NeuroD and NF-L were expressed. After exposure to 50, 100, and 200 Hz electromagnetic fields, the proliferation of mesenchymal stem cells was inhibited (FIG. 3), from which it could be seen that the differentiation of mesenchymal stem cells was induced. Moreover, the expression of Nestin was decreased only with the effects of electromagnetic fields in media without growth factors (FIG. 5). After exposure to electromagnetic fields, the morphology of mesenchymal stem cells was changed (FIG. 4), and the expression of neural stem cell markers such as Nestin and MAP2 was detected (FIGS. 5 to 7). Similar results were obtained from umbilical cord-derived mesenchymal stem cells (FIG. 9A) and adipose-derived mesenchymal stem cells (FIG. 9B) in addition to bone marrow-derived mesenchymal stem cells. Moreover, in the embodiment of the present invention, it could be seen that after exposure to electromagnetic fields, various types of mesenchymal stem cells markers such as neurons (MAP2), astrocytes (GFAP), and oligodendrocytes (O4) were expressed (FIG. 8).

Moreover, in the embodiment of the present invention, it could be seen that dental pulp stem cells could differentiate into neural cell by exposure to electromagnetic fields. The expression of neuronal differentiation markers and the formation of neurites were found in cells exposed to 50 Hz (1 mT) and 100 Hz (4 mT) electromagnetic fields.

Furthermore, the method of the present invention is to induce differentiation of mesenchymal stem cells and adult stem cells into neural cells using electromagnetic fields and can induce neuronal differentiation even under growth medium conditions.

As growth media, nonhematopoietic stem cell media from Miltenyi were used and cultured for 10 days. All mesenchymal stem cells used in the experiment can be cultured at 37° C. and 5% carbon dioxide atmosphere in nonhematopoietic stem cell media.

Figure 10:
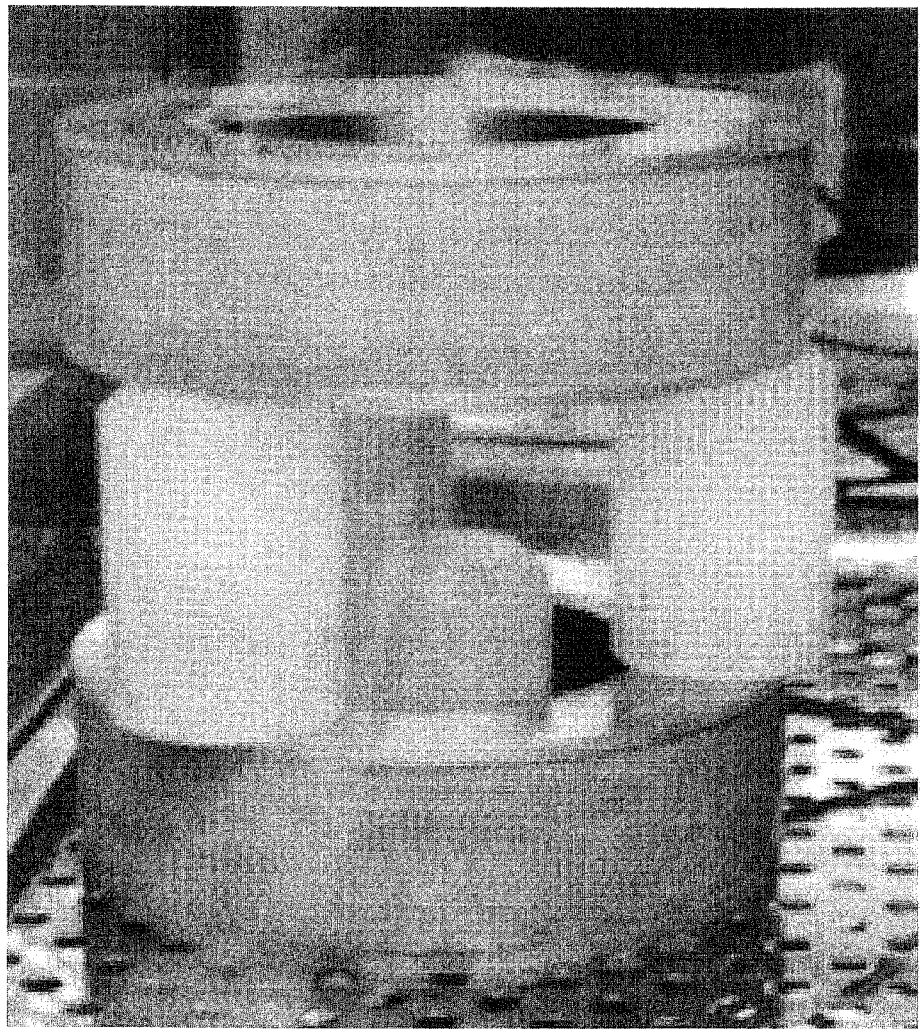
FIG. 10 shows the implementation of an electromagnetic field generator for differentiation of adult stem cells in accordance with an embodiment of the present invention.

An electromagnetic field generator for differentiation of mesenchymal stem cells according to the present invention may be configured as shown in FIG. 10. Moreover, for those not shown in FIG. 10, various techniques well known to those skilled in the art may be further included, which are within the spirit and scope of the present invention.

Furthermore, the present invention relates to a composition for treatment of neurological diseases comprising the neural cells differentiated by the above method.

The composition of the present invention uses neural cells differentiated from mesenchymal stem cells as a raw material and thus is non-toxic and safe.

The composition for treatment of neurological diseases may comprise pharmaceutical compositions well known to those skilled in the art in addition to the neural cells of the present invention and may be provided in the form of various formulations, which are within the spirit and scope of the present invention.

The composition may be formulated into a unit dosage form suitable for administration to a patient, and the composition comprises an effective dose that can develop alveoli by one or several administrations. The formulation suitable for this purpose may preferably be injections such as injectable ampoules for parenteral administration. The injectable ampoule may be mixed with an injection fluid before use, and the injection fluid may include saline solution, glucose, mannitol, Ringer's solution, etc.

The pharmaceutical preparation may further comprise one or more pharmaceutically acceptable inert carriers, for example, in the case of injections, preservatives, anesthetics, solubilizers, stabilizers, etc. and in the case of topical administration forms, bases, excipients, lubricants, preservatives, etc. in addition to the effective ingredient.

The composition or pharmaceutical preparation of the present invention prepared in the above manner may be administered in combination with other stem cells used for transplantation or other uses or in the form of a mixture with such stem cells by administration methods typically used in the art and may preferably be grafted or transplanted directly into a patient's lung disease area or transplanted or injected directly to the patient's respiratory tract, but not limited thereto. Moreover, the administration may include non-surgical administration using a catheter or surgical administration such as injection or transplantation after thoracic incision, and the non-surgical administration using a catheter is more preferable.

The neurological diseases of the present invention include all cranial nerve diseases such as Alzheimer's disease, depression, Parkinson's disease, cerebral infarction, cerebral hemorrhage, spinal cord injuries, etc., and the neural cells or neural stem cells differentiated according to the present invention recover the functions of neural cells in neurological diseases and can function as a therapeutic agent for neurological diseases.

Next, the present invention will be described in more detail with reference to examples. However, the following examples are provided only for the purpose of illustrating the present invention, and the present invention is not limited by the following examples.

Reference Example 1

Isolation of Umbilical Cord-Derived Mesenchymal Stem Cells and Culture of Bone Marrow and Adipose Derived Mesenchymal Stem Cells Human umbilical cord expelled during childbirth was washed with phosphate buffer solution 3 times, and Wharton's jelly left after removal of smooth muscle and epithelium around blood vessels was cut into 3 mm×3 mm, placed in a culture vessel, and left in an incubator at 37° C. for about 4 hours such that the tissues were attached to the bottom of the vessel. When Dulbecco's Modification of Eagle's Medium (DMEM) containing 10% fetal bovine serum (FBS) was added to the culture vessel and cultured for 1 week, cells were isolated from the Wharton's jelly of the umbilical cord, and when more than 80% of cells were proliferated on the bottom of the culture vessel, the subculture was performed to use the subcultured cells as a cell source.

Mesenchymal stem cells (passage 2) from bone marrow were purchased from Lonza (Lonza, Walkersville, Md., USA) and mesenchymal stem cells from adipose were purchased from Invitrogen (Invitrogen, Carlsbad, Calif., USA). The cells were cultured in NH (nonhematopoietic) stem cell medium (Miltenyi Biotech, Bergisch Gladbach, Germany) supplemented with 100 U/ml of penicillin, 100 μg/ml of streptomycin (Invitrogen, Carlsbad, Calif., USA) at 37° C. in a 5% $CO_2$ humidified atmosphere. The culture medium was changed twice a week. For subculture, cells were detached with accutase (Innovative Cell Tech., San Diego, Calif., USA) and passaged at a plate ratio of 1:4 after cells had reached 70-80% confluence. In this study the hBM-MSCs mostly were used at passages 4-6 for maintenance of sternness. Under normal expansion conditions, we cultured the hBM- MSCs in NH media, whereas we switched to DMEM media containing low glucose and FBS for the experiment.

Reference Example 2

Primary Culture of Dental Pulp Cells

Human tooth extracted by surgical operation was placed in 20 ml of α-MEM medium (Welgene, Korea) containing 200 μl of antibiotic/antimycotic and 10 μl of gentamycin, stored in an ice box containing ice, and sent to the laboratory.

Dental pulp tissues were obtained from the tooth after incision and placed in 3 ml of 1500 U collagenase solution containing 1% (v/v) serum. The resulting solution was stirred in a $CO_2$ incubator maintained at 37° C. for 90 minutes to loosen cells and tissues. Then, all tissues and enzymes were collected, placed in 20 ml of α-MEM medium containing 10% FBS, pipetted about 30 times, and then centrifuged at 800 rpm for 5 minutes. The supernatant was discarded and the remaining cells were inoculated into a 100 mm dish containing 10 ml of α-MEM medium containing 10% (v/v) FBS and cultured in a $CO_2$ incubator maintained at 37° C. for 10 days, while replacing the medium every 3 days.

Example 1

Capacity to Induce Differentiation of Mesenchymal Stem Cells into Neural Cells Using 50 to 200 Hz Electromagnetic Waves at Flux Density of 1 mT This example relates to a method for inducing differentiation of mesenchymal stem cells into neural cells using electromagnetic fields, and this method can induce neuronal differentiation even under growth medium conditions. The capacity of differentiation of mesenchymal stem cells was maintained using nonhematopoietic stem cell media. Bone marrow-derived mesenchymal stem cells used in the experiment were obtained from Lonza, fat-derived mesenchymal stem cells were obtained from Invitrogen, and umbilical cord-derived mesenchymal stem cells were isolated according to the method described in Reference Example 1. All stem cells were cultured at 37° C. and 5% carbon dioxide atmosphere.

50 Hz electromagnetic waves at 1 mT were exposed to the mesenchymal stem cells for 7 days and immunohistochemically stained to observe the results. As can be seen from FIG. 1, as a result of immunohistochemical staining, it was observed that the expression of MAP-2, tau, and syntaxin-1 was significantly increased at 1 mT and 50 Hz and the expression was not detected at 10 mT with the same frequency. It was determined that the cells were differentiated only at specific frequency and flux density.

Moreover, as shown in FIG. 2, it could be found that neuronal mRNAs such as NeuroD and NF-L were expressed after the differentiation induced by exposure to low-frequency electromagnetic waves for 7 days.

Furthermore, to identify the effects of electromagnetic fields on the differentiation of bone marrow-derived mesenchymal stem cells, bone marrow-derived mesenchymal stem cells (BM-MSC) were cultured in NH media, the components of the media were replaced with low glucose DMEM (LD-MEM) supplemented with 10% (v/v) fetal bovine serum and 25 mM ascorbic acid during exposure to electromagnetic fields, and then the mesenchymal stem cells were exposed to electromagnetic fields. The bone marrow-derived mesenchymal stem cells (BM-MSC) were exposed to 50 Hz electromagnetic fields at 1 mT for 12 days and subcultured once during the exposure. EBM media containing growth factors were used as a positive control, and RT-PCR and immunohistochemistry were performed by a method well known in the art to identify the expression of genes.

Figure 4:
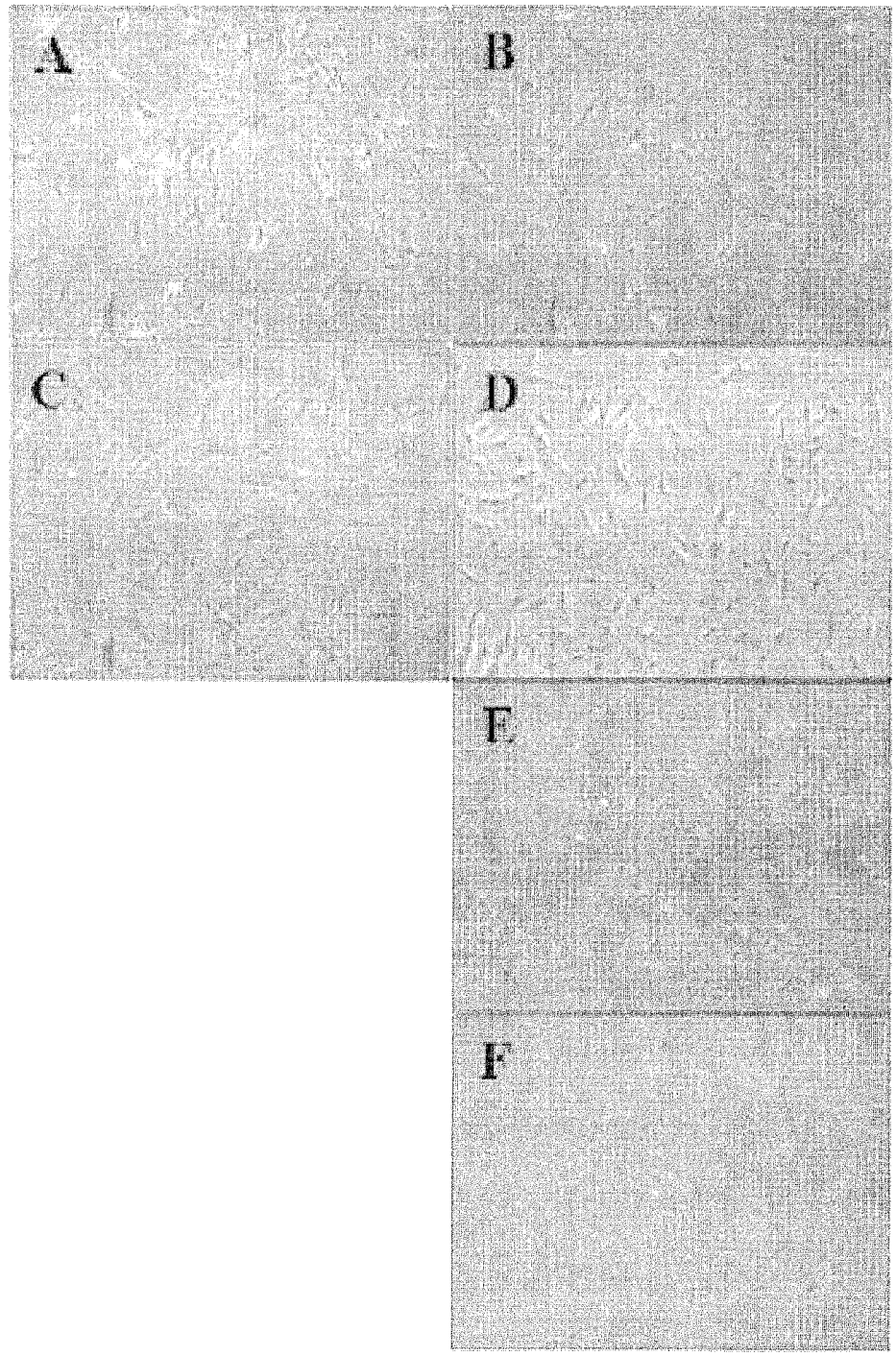
FIG. 4 shows the results of morphological changes observed using an optical microscope (A and C are controls, B and D were obtained after exposure of bone marrow-derived mesenchymal stem cells to 50 Hz electromagnetic fields, E was obtained after exposure to 100 Hz electromagnetic fields, F was obtained after exposure to 200 Hz electromagnetic fields, A and B were cultured in EGM media, and C, D, E and F were cultured in LDMEM media).
Figure 5:
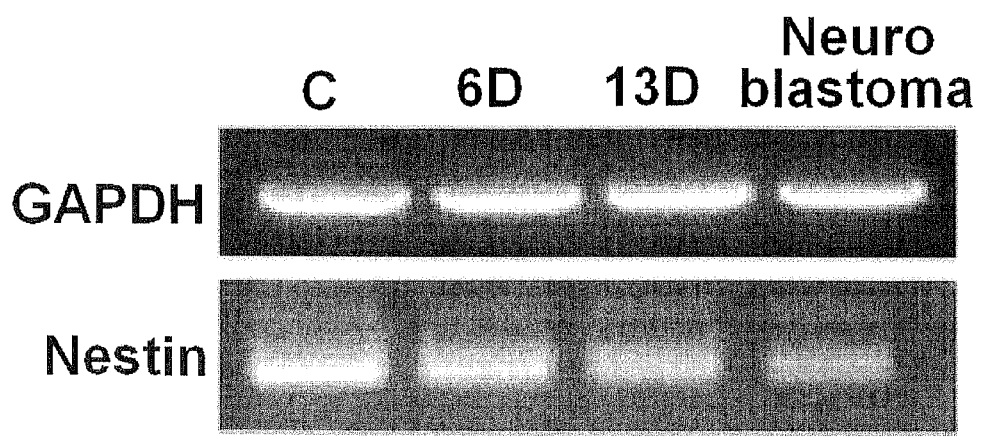
FIG. 5 shows a decrease in expression of Nestin, a mesenchymal stem cell marker, by 50 Hz electromagnetic fields.

As a result, as shown in FIGS. 4 and 5, it could be observed that the expression of Nestin, a mesenchymal stem cell marker, was decreased and the morphology of mesenchymal stem cells was changed. This means that bone marrow-derived mesenchymal stem cells (BM-MSC) differentiate into neuron-like cells.

Moreover, as a result of analyzing the gene expression, it could be found that Nestin, a neural stem cell marker, and MAP2, which was expressed at the beginning of the differentiation of neural cells, were expressed (FIGS. 5 to 7).

Similar results were obtained from umbilical cord-derived stem cells (FIG. 9A) and fat-derived stem cells (FIG. 9B) in addition to bone marrow-derived stem cells.

Example 2

Effects of 1 mT Electromagnetic Waves on Neuronal Differentiation of Dental Pulp Stem Cells FIG. 10 shows an electromagnetic field generator for differentiation of adult stem cells in accordance with an embodiment of the present invention. Dental pulp stem cells were primarily cultured in the same manner as Reference Example 1, the used media were removed, and the cultured cells were washed once with 10 ml of phosphate buffered saline (PBS). The washed cells were added to 1 ml of solution containing 0.05% (v/v) trypsin and 0.01% (v/v) EDTA and treated at 37° C. for 5 minutes such that the cells were placed on the bottom of the dish and suspended in the solution. The cell solution was mixed with 15 ml of α-MEM medium containing 10% (v/v) FBS and centrifuged at 1,000 rpm for 5 minutes, thus collecting only the cells. These cells were cultured in a $CO_2$ incubator for 5 subcultures and then used in the experiment.

These cells were inoculated into a 60 mm culture dish of α-MEM medium containing 10% (v/v) FBS at a density of $1\times10^5$ cells/dish and cultured in a $CO_2$ incubator maintained at 37° C. for 5 days, while replacing the medium every 3 days.

At this time, the electromagnetic field generator was mounted in the incubator, the 60 mm dish was placed on the electromagnetic field generator and cultured by applying electromagnetic waves of 0 Hz (non-radiation group), 50 Hz (1 mT), and 100 Hz (1 mT) frequencies to form electromagnetic fields.

Figure 11:
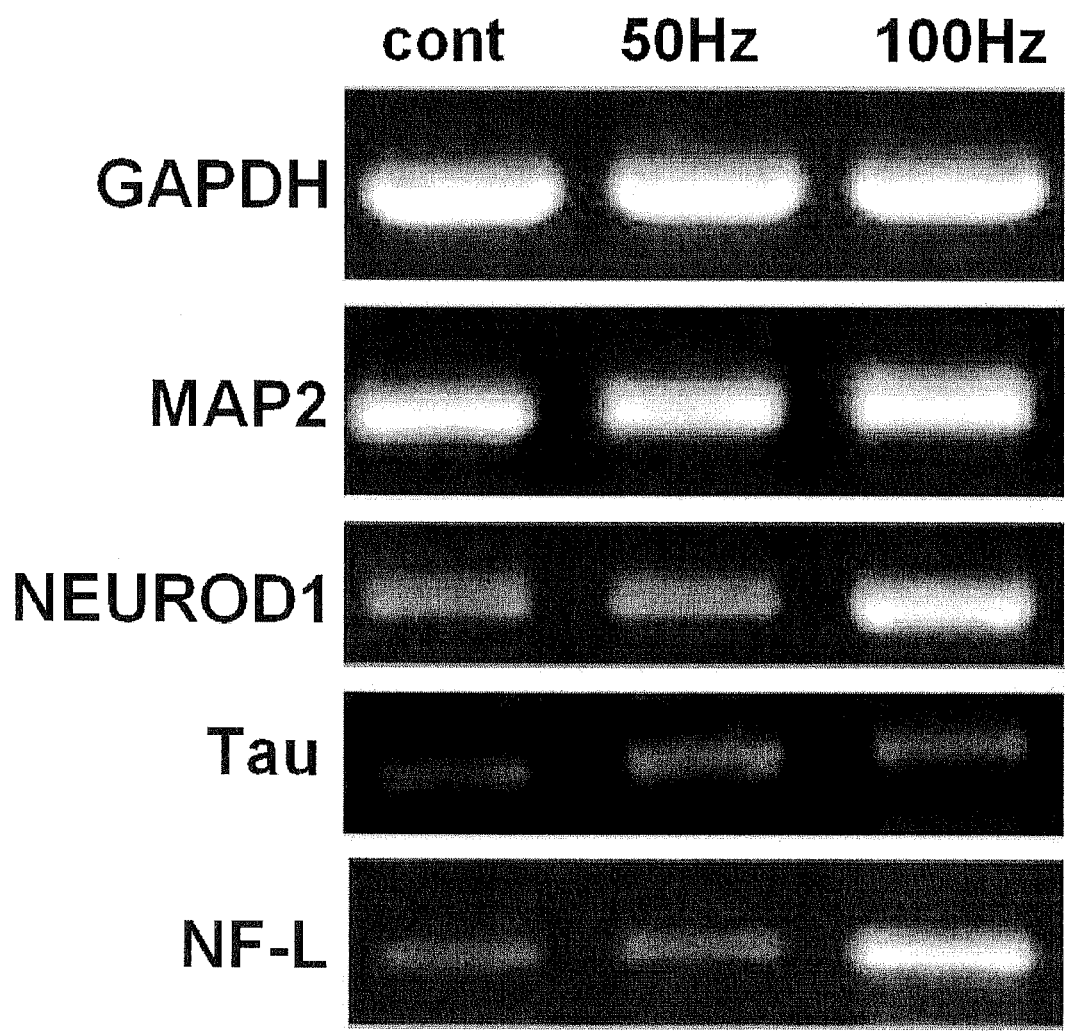
FIG. 11 shows the results of expression of neuronal markers after radiation of 50 Hz (1 mT) and 100 Hz (1 mT) electromagnetic field to dental pulp stem cells at the $4^{th}$ subculture, obtained by mRNA analysis.

The cultured cells were collected and subjected to mRNA analysis. As a result, it could be seen that the expression of neuronal differentiation markers such as MAP2, NeuroD1, and DCX was increased at 100 Hz (1 mT), compared to the non-radiation group, from which it could be concluded that the dental pulp stem cells were differentiated into neural cells (FIG. 11).

Example 3

Effects of 4 mT Electromagnetic Waves on Neuronal Differentiation of Dental Pulp Stem Cells The cultured dental pulp cells were subcultured 7 times, inoculated into a 60 mm culture dish of α-MEM medium containing 10% (v/v) FBS at a density of $1\times10^5$ cells/dish and cultured in a $CO_2$ incubator maintained at 37° C. for 5 days, while replacing the medium every 3 days.

At this time, the electromagnetic field generator was mounted in the incubator, the 60 mm dish was placed on the electromagnetic field generator and cultured by applying electromagnetic waves of 0 Hz (non-radiation group), 50 Hz (1 mT), and 100 Hz (4 mT) frequencies to form electromagnetic fields.

Figure 12:
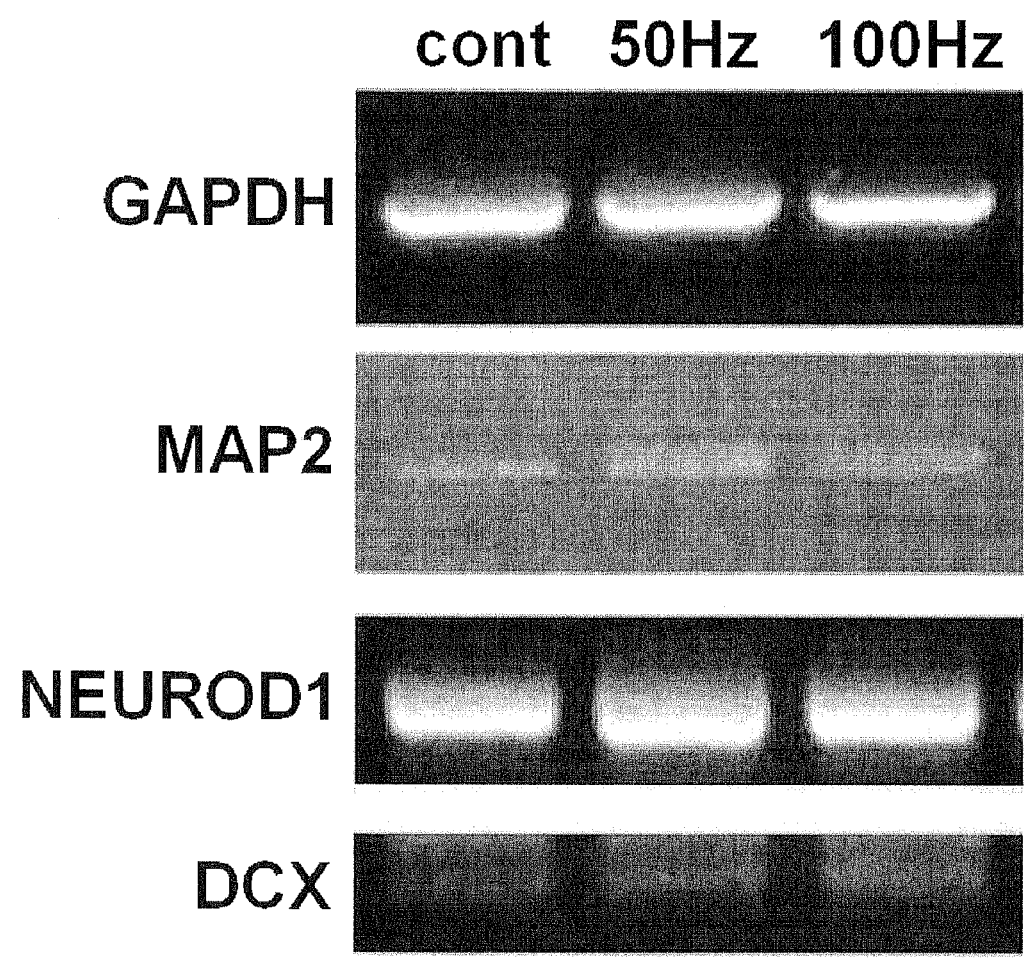
FIG. 12 shows the results of expression of neuronal markers after radiation of 50 Hz (1 mT) and 100 Hz (4 mT) electromagnetic field to dental pulp stem cells at the $7^{th}$ subculture, obtained by mRNA analysis.

The cultured cells were collected and subjected to mRNA analysis. As a result, it could be seen that the expression of neuronal differentiation markers such as MAP2, NeuroD1, and DCX were increased at 50 Hz (1 mT) and 100 Hz (4 mT), compared to the non-radiation group, from which it could be concluded that the dental pulp stem cells were differentiated into neural cells (FIG. 12).

Figure 13:
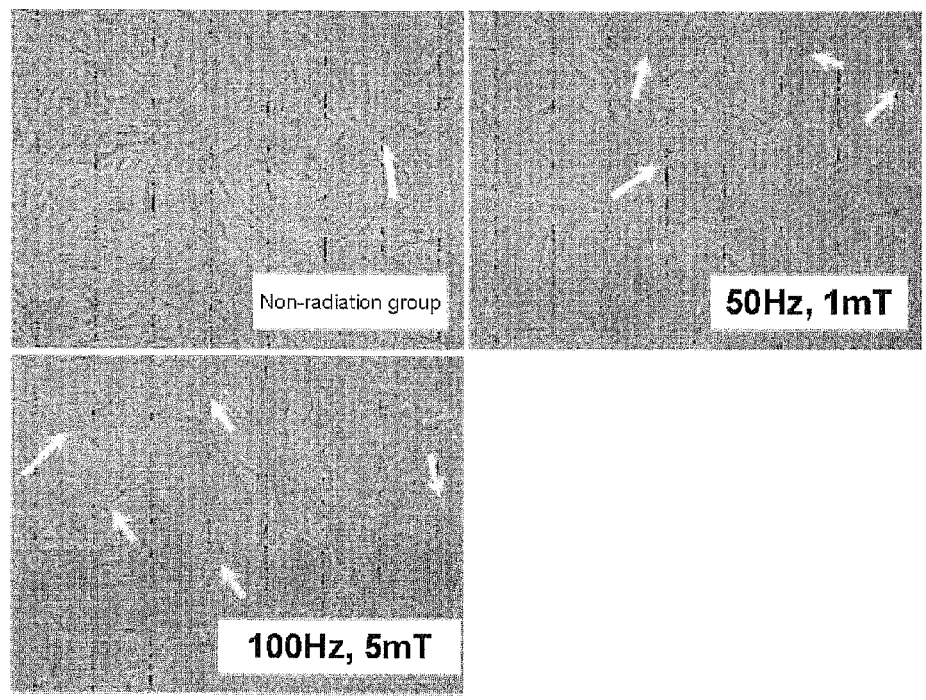
FIG. 13 shows the results of morphological changes of cells after radiation of 50 Hz (1 mT) and 100 Hz (4 mT) electromagnetic field to dental pulp stem cells at the $7^{th}$ subculture.

The morphological changes of cells were observed using an optical microscope and, as a result, it could be seen that many neurites (shown by arrows) were formed at 50 Hz (1 mT) and 100 Hz (4 mT) (FIG. 13).

The method and apparatus for differentiation of stem cells using electromagnetic fields according to the present invention can induce differentiation of adult stem cells into neural cells using low-frequency electromagnetic fields, which makes it possible to easily obtain neural cells or neural stem cells, which are difficult to obtain, can induce neuronal differentiation even under conditions of low-cost media, not with neuronal differentiation induction media which are expensive due to the addition of growth factors, and thus can be effectively used for the treatment of cranial nerve diseases such as Alzheimer's disease, depression, Parkinson's disease, cerebral infarction, cerebral hemorrhage, spinal cord injuries, etc.

The invention claimed is:

1. A method for differentiation of mesenchymal stem cells or dental pulp stem cells into neural cells comprising applying an electromagnetic field at a frequency of 50 to 200 Hz and a flux density of 1 to 5 mT to the mesenchymal stem cells or dental pulp stem cells.

2. The method of claim 1, wherein the neural cells comprises astrocytes or oligodendrocytes.

3. The method of claim 1, wherein the mesenchymal stem cells are derived from bone marrow, adipose, or umbilical cord.

* * * * *